(12) United States Patent
Motohara (10) Patent No.: US 11,857,166 B2
(45) Date of Patent: Jan. 2, 2024

(54) IMAGING UNIT AND ENDOSCOPE (71) Applicant: OLYMPUS CORPORATION, Tokyo (JP)

(72) Inventor: Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 743 days.

(21) Appl. No.: 17/028,336

(22) Filed: Sep. 22, 2020

(65) Prior Publication Data
US 2021/0006690 A1 Jan. 7, 2021

Related U.S. Application Data (63) Continuation of application No. PCT/JP2019/008971, filed on Mar. 6, 2019.

(30) Foreign Application Priority Data

Apr. 3, 2018 (JP) .................................. 2018-071719

(51) Int. Cl.
*H05K 1/14* (2006.01)
*A61B 1/05* (2006.01)
*H05K 1/11* (2006.01)

(52) U.S. Cl.
CPC .............. *A61B 1/051* (2013.01); *H05K 1/115* (2013.01); *H05K 1/147* (2013.01); *H05K 2201/10015* (2013.01); *H05K 2201/10151* (2013.01); *H05K 2201/10757* (2013.01)

(58) Field of Classification Search
CPC ... H05K 1/14–148; H05K 2201/10141; H05K 2201/10757; A61B 1/051
See application file for complete search history.

(56) References Cited

U.S. PATENT DOCUMENTS

2004/0130640 A1* 7/2004 Fujimori ............... H01L 23/481
257/E31.127
2005/0277808 A1* 12/2005 Sonnenschein ...... A61B 1/0607
600/153
(Continued)

FOREIGN PATENT DOCUMENTS

JP 5905980 B1 4/2016
JP 5972415 B1 8/2016
(Continued)

OTHER PUBLICATIONS

Abstract only of JP 2016-150191A (publication of JP 5972415 B1).
(Continued)

*Primary Examiner* — Hoa C Nguyen
(74) *Attorney, Agent, or Firm* — Scully, Scott, Murphy & Presser, P.C.

(57) ABSTRACT

An imaging unit includes: a semiconductor package including an optical system, an imaging sensor, and connection terminals; a rigid substrate including first connection lands respectively connected to the connection terminals; and an electronic component mount region including second connection lands on which a capacitor is mounted, and an inner lead mount region including third connection lands; and a flexible printed board including inner leads extended from one end of the flexible printed board in a bent manner and respectively connected to the third connection leads in the inner lead mount region; and cable connection leads arranged on another end of the flexible printed board and respectively connected to the inner leads. The rigid substrate and the flexible printed board are arranged in a projection plane in an optical axis direction of the semiconductor package. The third connection lands are arranged along one side of the rigid substrate.

7 Claims, 5 Drawing Sheets

(56) References Cited

U.S. PATENT DOCUMENTS

| | | | | |
|---|---|---|---|---|
| 2009/0306475 A1* | 12/2009 | Yamamoto | ........... | H05K 1/0243 600/110 |
| 2013/0008694 A1* | 1/2013 | Takamatsu | ......... | A61B 1/00027 174/250 |
| 2013/0244453 A1* | 9/2013 | Sakamoto | ............ | H01R 12/721 439/55 |
| 2016/0274350 A1* | 9/2016 | Aizenfeld | ............... | H04N 23/51 |
| 2017/0164818 A1 | 6/2017 | Ishikawa et al. | | |
| 2018/0049628 A1 | 2/2018 | Motohara et al. | | |
| 2018/0070799 A1* | 3/2018 | Sekido | ................... | A61B 1/051 |
| 2019/0038117 A1* | 2/2019 | Motohara | .............. | H04N 23/00 |
| 2019/0069767 A1 | 3/2019 | Mikami et al. | | |
| 2020/0049972 A1* | 2/2020 | Igarashi | ............ | H01L 27/14636 |

FOREIGN PATENT DOCUMENTS

| | | |
|---|---|---|
| JP | 2017-023234 A | 2/2017 |
| WO | 2016/111075 A1 | 7/2016 |
| WO | 2016/194074 A1 | 12/2016 |
| WO | 2017/130886 A1 | 8/2017 |
| WO | 2017/199406 A1 | 11/2017 |

OTHER PUBLICATIONS

Abstract only of JP 2017-023210 A (publication of JP 5905980 B1).
International Search Report dated May 28, 2019 received in PCT/JP2019/008971.

* cited by examiner

IMAGING UNIT AND ENDOSCOPE

This application is a continuation of PCT international application Ser. No. PCT/JP2019/008971, filed on Mar. 6, 2019 which designates the United States, incorporated herein by reference, and which claims the benefit of priority from Japanese Patent Applications No. 2018-071719, filed on Apr. 3, 2018, incorporated herein by reference.

BACKGROUND

The present disclosure relates to an imaging unit and an endoscope.

In the medical field and the industrial field, endoscopes have been widely used for various examinations. Among the endoscopes, a medical endoscope has been widely used because, by inserting a thin and elongated flexible insertion portion that is provided with an imaging apparatus at a distal end thereof into a subject, such as a patient, the medical endoscope is able to acquire an in-vivo image inside the subject without making an incision in the subject and further able to perform curative treatment by causing a treatment tool to protrude from the distal end of the insertion portion if needed.

In the medical endoscope, for purpose of reduction in loads on the patient or the like, techniques for reducing a size and a diameter of the insertion portion have been proposed. For example, an imaging unit has been disclosed in which a lens unit is bonded and fixed with adhesive resin to a cover glass that covers an imaging surface of an imaging element, a capacitor is mounted on a surface opposite to the imaging surface of the imaging element, and a cable is connected via a circuit substrate (for example, see Japanese Patent No. 5972415 and Japanese Patent No. 5905980).

SUMMARY

According to one aspect of the present disclosure, there is provided an imaging unit including: a semiconductor package including an optical system, an imaging sensor configured to convert an optical image formed by the optical system to an image signal, and a plurality of connection terminals provided on a back surface, each of the plurality of connection terminals having a function; a rigid substrate including a plurality of first connection lands provided on a front surface of the rigid substrate, the plurality of first connection lands being respectively connected to the plurality of connection terminals; and an electronic component mount region provided on a back surface of the rigid substrate, the electric component mount region including a plurality of second connection lands on which a capacitor is mounted, and an inner lead mount region provided on the back surface of the rigid substrate, the inner lead mount region including a plurality of third connection lands; and a flexible printed board extending in an optical axis direction of the imaging sensor, the flexible printed board including a plurality of inner leads extended from one end of the flexible printed board in a bent manner and respectively connected to the third connection leads in the inner lead mount region; and a plurality of cable connection leads arranged on another end of the flexible printed board and respectively connected to the plurality of inner leads, wherein the rigid substrate and the flexible printed board are arranged in a projection plane in an optical axis direction of the semiconductor package, and the plurality of third connection lands are arranged along one side of the rigid substrate.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, as modes for carrying out the present disclosure (hereinafter, referred to as an "embodiment"), an endoscope system including an imaging unit will be described. The present disclosure is not limited by the embodiment below. Further, in description of the drawings, the same components are denoted by the same reference symbols. Furthermore, it is necessary to note that the drawings are schematic, and relations between thicknesses and widths of the components, ratios among the components, and the like may be different from actual ones. Moreover, the drawings may include portions that have different dimensional relations or ratios.

Figure 1:
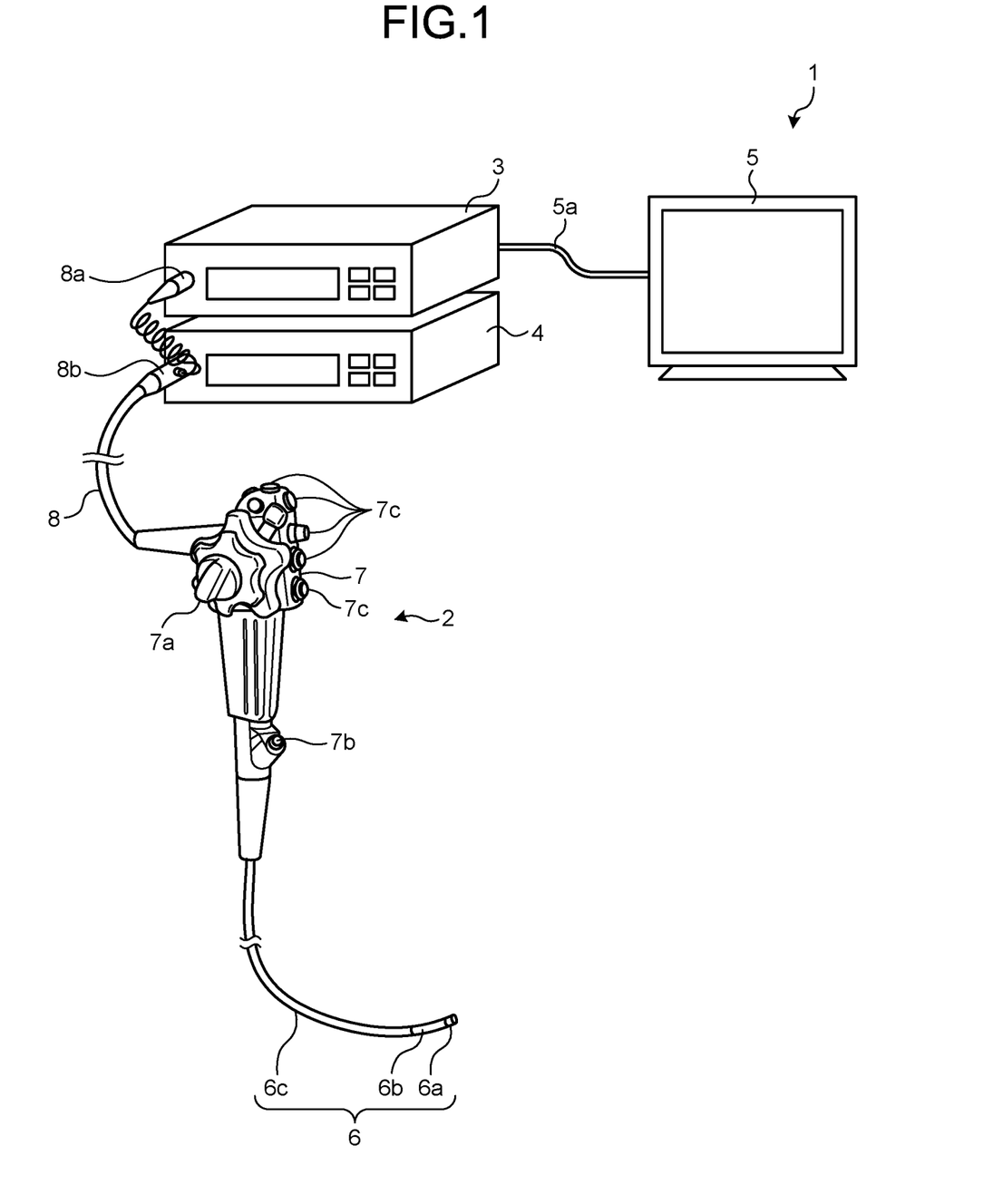
FIG. 1 is a diagram schematically illustrating an overall configuration of an endoscope system according to an embodiment.

FIG. 1 is a diagram schematically illustrating an overall configuration of an endoscope system 1 according to an embodiment. As illustrated in FIG. 1, the endoscope system 1 according to the embodiment includes an endoscope 2 that is inserted into a subject, that captures an in-vivo image of the subject, and that generates an image signal inside the subject, an information processing device 3 that performs predetermined image processing on the image signal captured by the endoscope 2 and controls each of components of the endoscope system 1, a light source device 4 that generates illumination light of the endoscope 2, and a display device 5 that displays an image of the image signal that has been subjected to the image processing by the information processing device 3.

The endoscope 2 includes an insertion portion 6 that is to be inserted into the subject, operating unit 7 that is arranged on a proximal end portion side of the insertion portion 6 and that is gripped by an operator, and a flexible universal cord 8 that is extended from the operating unit 7.

The insertion portion 6 is realized by an illumination fiber (light guide cable), an electrical cable, an optical fiber, and the like. The insertion portion 6 includes a distal end portion 6a in which an imaging unit (to be described later) is incorporated, a bending portion 6b that is configured with a plurality of bending pieces and that is freely bendable, and a flexible tube portion 6c that is arranged on a proximal end portion side of the bending portion 6b. In the distal end portion 6a, illumination channels, which are communicated with illumination fibers for illuminating the inside of the subject via an illumination lens, and a treatment tool channel, in which a treatment tool is inserted, are arranged.

The operating unit 7 includes a bending knob 7a that causes the bending portion 6b to bend in the vertical direction and in the horizontal direction, a treatment tool insertion portion 7b through which a treatment tool, such as a biopsy forceps or a laser scalpel, is inserted into a body cavity of the subject, and a plurality of switch portions 7c for performing operation on peripheral devices, such as the information processing device 3, the light source device 4, an air supply device, a water supply device, and a gas supply device. The treatment tool inserted through the treatment tool insertion portion 7b is exposed from an opening at a distal end of the insertion portion 6 via the treatment tool channel that is arranged inside the insertion portion 6.

The universal cord 8 is configured with an illumination fiber, a cable, and the like. The universal cord 8 is branched at a proximal end thereof such that an end portion of one branch serves as a connector 8a and a proximal end of the other branch serves as a connector 8b. The connector 8a is freely attachable to and detachable from a connector of the information processing device 3. The connector 8b is freely attachable to and detachable from the light source device 4. The universal cord 8 propagates illumination light emitted by the light source device 4 to the distal end portion 6a via the connector 8b and the illumination fiber. Further, the universal cord 8 transmits an image signal captured by the imaging unit (to be described later) to the information processing device 3 via a cable and the connector 8a.

The information processing device 3 performs predetermined image processing on the image signal output from the connector 8a and controls the entire endoscope system 1.

The light source device 4 is configured with a light source that emits light, a condenser lens, and the like. The light source device 4 emits light from the light source and supplies the light as illumination light for illuminating the inside of the subject as an imaging object to the endoscope 2 that is connected via the connector 8b and the illumination fiber in the universal cord 8, under the control of the information processing device 3.

The display device 5 is configured with a display or the like made with liquid crystal or organic electro luminescence (EL). The display device 5 displays, via a video cable 5a, various kinds of information including an image that is subjected to the predetermined image processing by the information processing device 3. Therefore, an operator is able to observe a desired position inside the subject and determine symptoms at the position by operating the endoscope 2 while viewing the image (in-vivo image) displayed by the display device 5.

Figure 2:
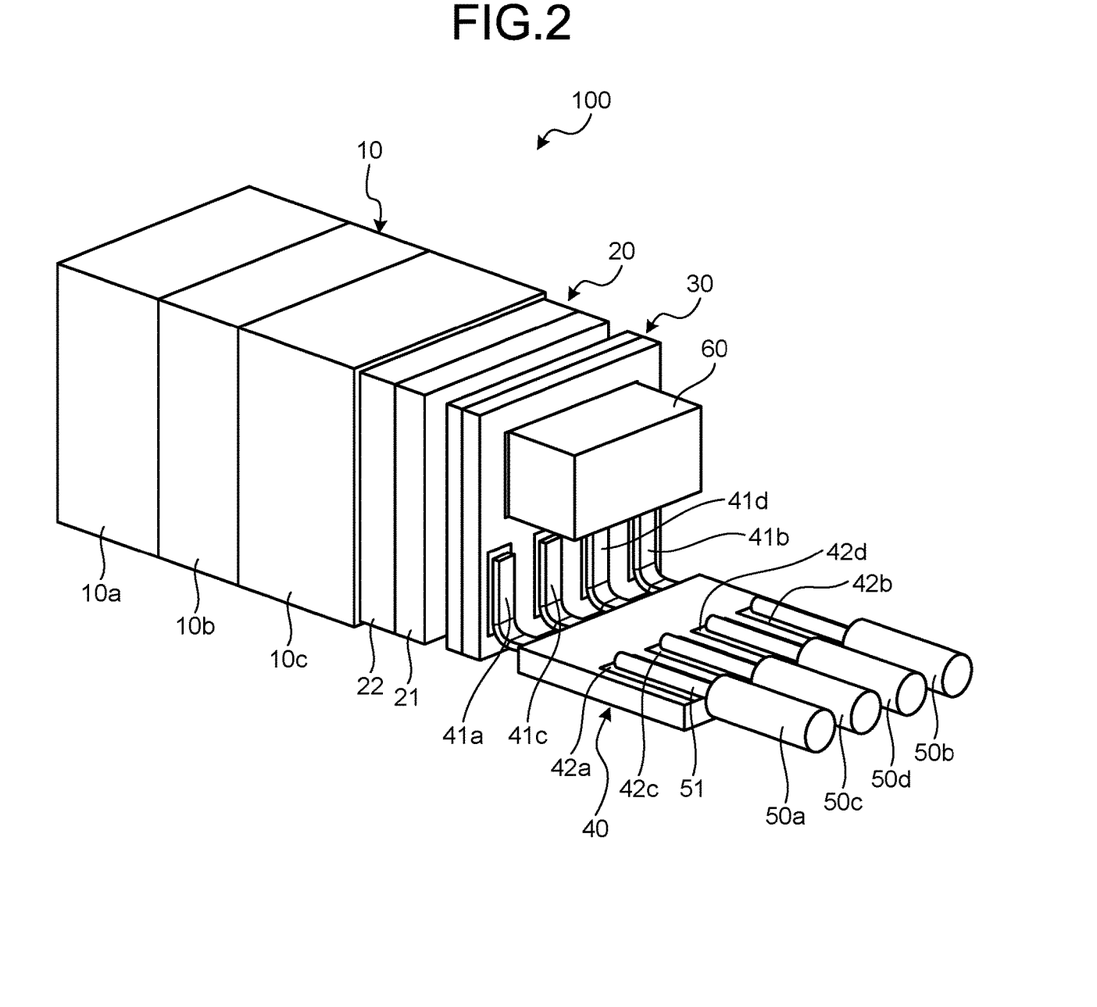
FIG. 2 is a perspective view of an imaging unit that is arranged at a distal end portion of an endoscope illustrated in FIG. 1.
Figure 3:
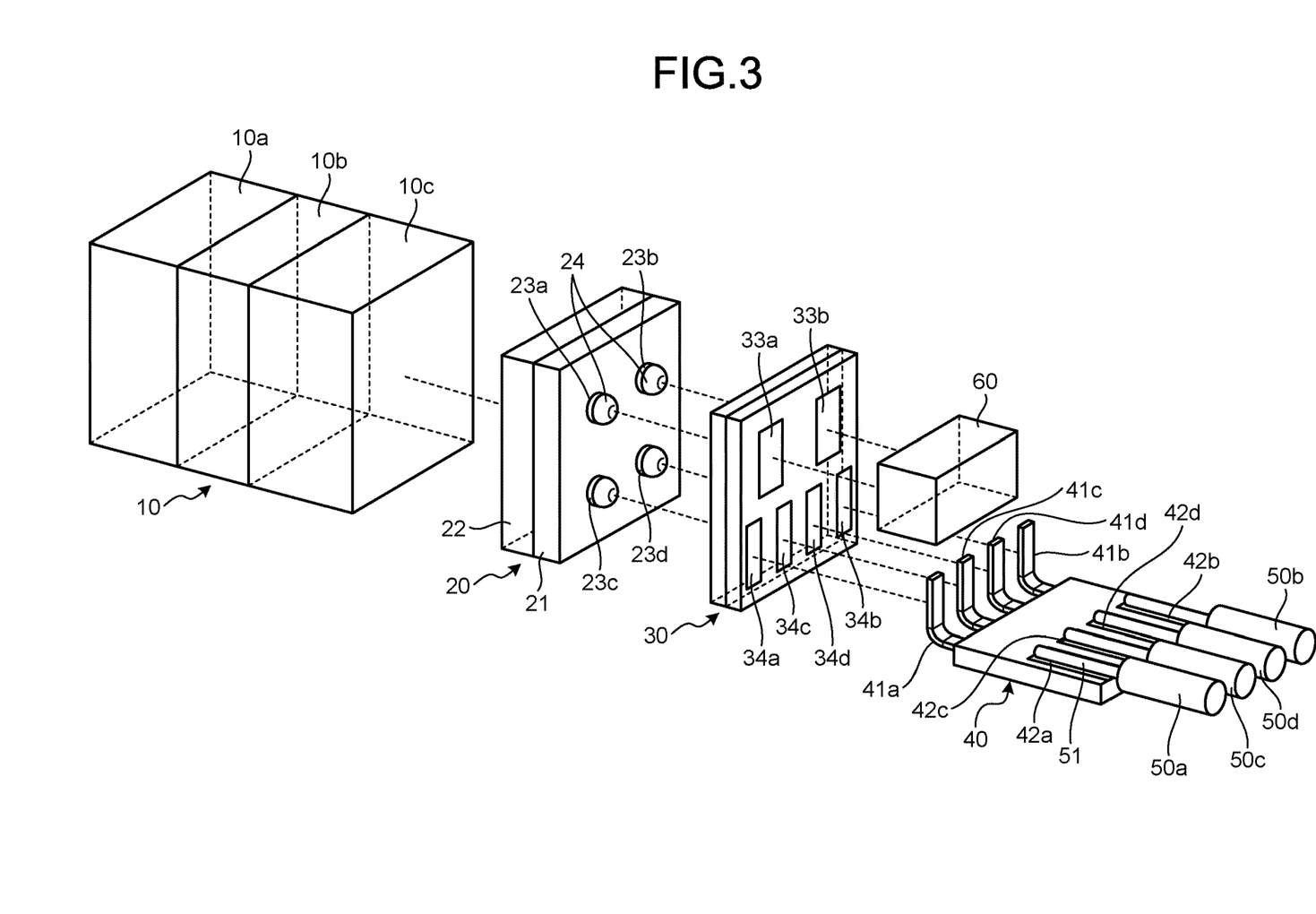
FIG. 3 is an exploded perspective view of the imaging unit illustrated in FIG. 2.

An imaging unit 100 used in the endoscope system 1 will be described in detail below. FIG. 2 is a perspective view of the imaging unit 100 that is arranged in the distal end portion 6a of the endoscope 2 illustrated in FIG. 1. FIG. 3 is an exploded perspective view of the imaging unit 100 illustrated in FIG. 2. In the present specification, a side at the distal end portion 6a of the endoscope 2 will be referred to as a distal end side, and a side at which cables 50 are extended will be referred to as a proximal end side.

The imaging unit 100 includes an optical system 10 that includes a plurality of lenses 10a to 10c, a semiconductor package 20 that includes, on a front surface thereof, an imaging element configured to convert an optical image formed by the optical system 10 to an image signal and includes, on a back surface thereof, four connection terminals 23a to 23d to which a power supply function, a grounding function, a first communication function, and a second communication function are respectively assigned, a rigid substrate 30 that includes, on a front surface thereof, four connection lands 31a to 31d (see FIG. 5, where 31b and 31d are not illustrated) respectively connected to the four connection terminals 23a to 23d and includes, on a back surface thereof, an electronic component mount region R1 in which two second connection lands 33a and 33b for mounting a capacitor 60 are formed and an inner lead mount region R2 in which four third connection lands 34a to 34d are formed, and a flexible printed board 40 that includes four inner leads 41a to 41d, which are extended from one end of the flexible printed board 40 in a bent manner and respectively connected to the third connection lands 34a to 34d in the inner lead mount region R2, includes four cable connection lands 42a to 42d, which are arranged on the other end of the flexible printed board 40 and respectively connected to the four inner leads 41a to 41d, and extends in an optical axis direction of the imaging element.

The lenses 10a to 10c have rectangular outer shapes that are approximately the same as a shape of the semiconductor package 20 (to be described later), and are bonded together with optical adhesive or held by a lens frame (not illustrated).

The semiconductor package 20 is configured such that a cover glass 22 is attached to an imaging element 21. Light that has entered the objective optical system 10 enters the front surface (light receiving surface) of the imaging element 21 via the cover glass 22. The connection terminals 23a to 23d and bump 24 formed with solder or the like are formed on a back surface of the light receiving surface of the imaging element 21. It is preferable that the semiconductor package 20 is a chip scale package (CSP) that is obtained by performing wiring, electrode formation, resin sealing, and dicing on an imaging element chip at a wafer level such that the resulting size of the imaging element chip is the same as the size of the semiconductor package 20. The optical system 10 and the semiconductor package 20 are bonded together with optical adhesive or held and fixed via a lens barrel (not illustrated).

The power supply function, the grounding function, the first communication function, and the second communication function are respectively assigned to the connection terminals 23a, 23b, 23c, and 23d. The connection terminals 23a and 23b having the power supply function and the grounding function are arranged side by side. As illustrated in FIG. 3, in the embodiment, the connection terminal 23a in the upper left of the back surface of the semiconductor package 20 is used as a power supply terminal, the connection terminal 23b in the upper right is used as a ground terminal, the connection terminal 23c in the lower left is used as a first communication terminal, and the connection terminal 23d in the lower right is used as a second communication terminal. The first communication terminal and the second communication terminal are video signal output terminals or clock signal input terminals.

The rigid substrate 30 has a rectangular plate shape that is approximately the same as the shape of the semiconductor package 20 in the optical axis direction, and is configured with a ceramic substrate or a silicon substrate. The silicon substrate may include a circuit or a capacitor. The rigid substrate 30 includes, on the front surface side thereof, the four first connection lands 31a to 31d (see FIG. 5, where 31b and 31d are not illustrated) that are respectively connected to the four connection terminals 23a to 23d via the bumps 24 in the semiconductor package. Further, the rigid substrate 30 includes, on the back surface side, the electronic component mount region R1 in which the two second connection lands 33a and 33b for mounting the capacitor 60 and the inner lead mount region R2 in which the four third connection lands 34a to 34d are formed. The third connection lands 34a to 34d are arranged along one side of the rigid substrate 30 in the inner lead mount region R2.

Figure 4:
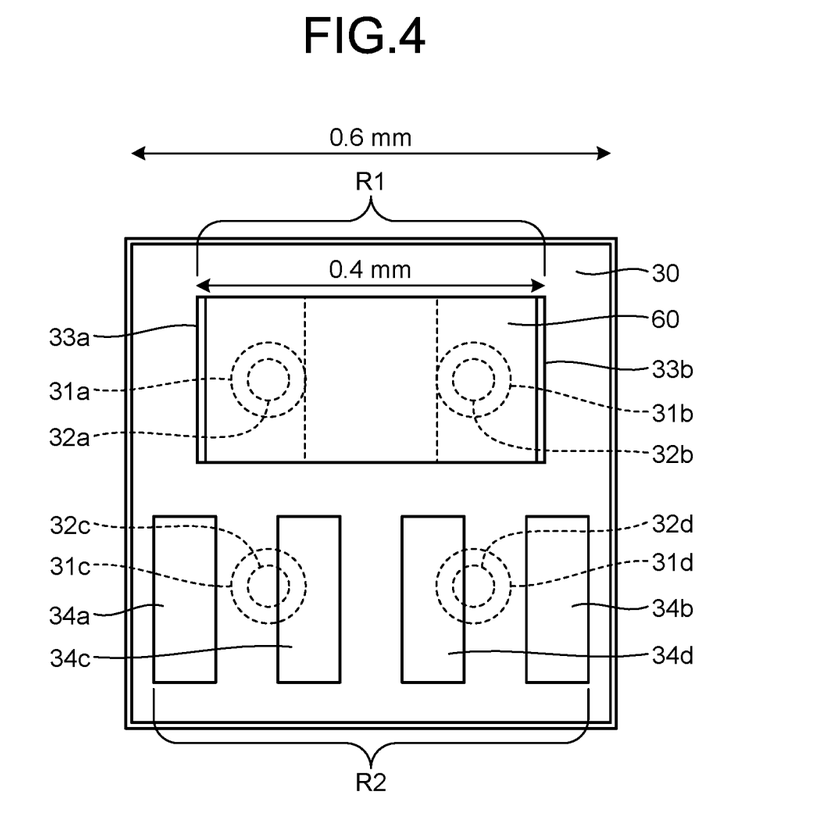
FIG. 4 is a back view of a rigid substrate illustrated in FIG. 2.
Figure 5:
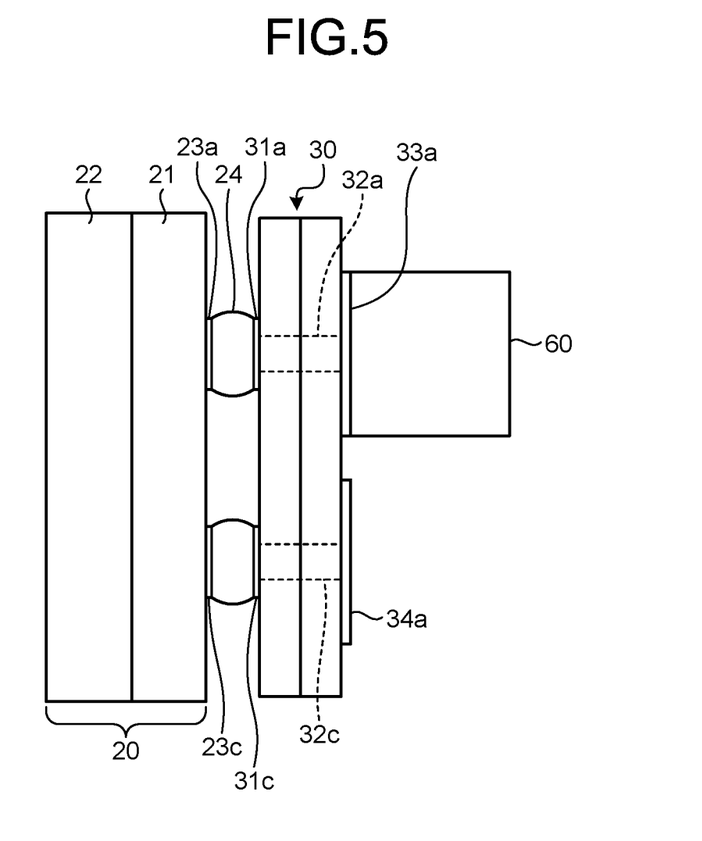
FIG. 5 is a side view of the imaging unit illustrated in FIG. 2.

The second connection lands 33a and 33b are connected to the first connection lands 31a and 31b through vias 32a and 32b. As illustrated in FIG. 4 and FIG. 5, the second connection lands 33a and 33b are formed just above the first connection lands 31a and 31b (overlapping positions in the optical axis direction), and are connected to the first connection lands 31a and 31b at minimum distances through the vias 32a and 32b. The capacitor 60 is connected to the connection terminals 23a and 23b at minimum distances through the second connection lands 33a and 33b, the vias 32a and 32b, the first connection lands 31a and 31b, and the bumps 24, so that it is possible to stably drive the imaging element 21.

The third connection lands 34a and 34b are connected to the first connection lands 31a and 31b through the vias 32a and 32b and wires (not illustrated).

The third connection lands 34c and 34d are connected to the first connection lands 31c and 31d through vias 32c and 32d. As illustrated in FIG. 4 and FIG. 5, the third connection lands 34c and 34d are formed just above the first connection lands 31c and 31d (overlapping positions in the optical axis direction), and connected to the first connection lands 31c and 31d at minimum distances through the vias 32c and 32d.

The flexible printed board 40 includes the four inner leads 41a to 41d that are extended in a bent manner from one end of the flexible printed board 40, and the four cable connection lands 42a to 42d arranged on the side opposite to the side where the inner leads 41a to 41d are extended. The flexible printed board 40 extends in the optical axis direction of the imaging element 21.

The inner leads 41a, 41b, 41c, and 41d are respectively connected to the third connection lands 34a, 34b, 34c, and 34d with conductive materials, such as solder (not illustrated).

The cable connection lands 42a, 42b, 42c, and 42d are respectively connected to the inner leads 41a, 41b, 41c, and 41d with wires (not illustrated). Core wires 51 of cables 50a, 50b, 50c, and 50d are respectively connected to the cable connection lands 42a, 42b, 42c, and 42d with conductive materials, such as solder (not illustrated).

The cable 50a is connected to the connection terminal 23a, which serves as the power supply terminal, via the cable connection land 42a, the inner lead 41a, the third connection land 34a, the second connection land 33a, the via 32a, and the first connection land 31a. The cable 50a is a power supply cable for supplying a power source to the capacitor 60 and the imaging element 21.

The cable 50b is connected to the connection terminal 23b, which serves as the ground terminal, via the cable connection land 42b, the inner lead 41b, the third connection land 34b, the second connection land 33b, the via 32b, and the first connection land 31b.

The cable 50c is connected to the connection terminal 23c, which serves as the first communication terminal, via the cable connection land 42c, the inner lead 41c, the third connection land 34c, the via 32c, and the first connection land 31c. The cable 50c is an image signal transmission cable for transmitting the image signal generated by the imaging element 21. The cable connection land 42c and the inner lead 41c are connected to each other at a minimum distance in the flexible printed board 40, and are also connected to the connection terminal 23c at a minimum distance in a projection plane in the optical axis direction of the semiconductor package 20; therefore, it is possible to transmit the image signal with reduced noise.

The cable 50d is connected to the connection terminal 23d, which serves as a clock signal input terminal, via the cable connection land 42d, the inner lead 41d, the third connection land 34d, the via 32d, and the first connection land 31d. The cable 50d is a clock signal transmission cable for transmitting a clock signal to the imaging element 21. The cable connection land 42d and the inner lead 41d are connected to each other at a minimum distance in the flexible printed board 40, and are also connected to the connection terminal 23d at a minimum distance in the projection plane in the optical axis direction of the semiconductor package 20.

The third connection lands 34c and 34d are formed just above the first connection lands 31c and 31d, connected to the first connection lands 31c and 31d at minimum distances through the vias 32c and 32d, and connected to the cables 50c and 50d by the inner leads 41c and 41d and the cable connection lands 42c and 42d. The image signal and the clock signal are transmitted at short distances, so that it is possible to obtain an image signal with reduced noise.

In the imaging unit 100, the inner leads 41a to 41d extending from an end surface of the flexible printed board 40 are connected in a bent manner to the third connection lands 34a to 34d, so that the flexible printed board 40 extends in the projection plane in the optical axis direction of the semiconductor package. Further, the cables 50a to 50d are connected to the cable connection lands 42a to 42d on the other side of the flexible printed board 40 that extends in the optical axis direction, and are arranged in the projection plane in the optical axis direction of the semiconductor package. Therefore, it is possible to reduce a diameter of the imaging unit 100 and ensure connection areas of the cables 50a to 50c, so that even when stress is applied to connection portions in accordance with operation of the bent portions, it is possible to maintain connection reliability.

An imaging unit according to the present disclosure is useful for an endoscope system whose diameter needs to be reduced.

According to the present disclosure, it is possible to stably drive an imaging element and reduce diameters of an imaging unit and an endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An imaging unit comprising:
a semiconductor package including
an optical system,
an imaging sensor configured to convert an optical image formed by the optical system to an image signal, and
a plurality of connection terminals provided on a back surface, each of the plurality of connection terminals having a function;
a rigid substrate including
a plurality of first connection lands provided on a front surface of the rigid substrate, the plurality of first connection lands being respectively connected to the plurality of connection terminals; and an electronic component mount region provided on a back surface of the rigid substrate, the electric component mount region including a plurality of second connection lands on which a capacitor is mounted, and an inner lead mount region provided on the back surface of the rigid substrate, the inner lead mount region including a plurality of third connection lands; and a flexible printed board extending in an optical axis direction of the imaging sensor, the flexible printed board including a plurality of inner leads extended from one end of the flexible printed board in a bent manner and respectively connected to the third connection leads in the inner lead mount region; and a plurality of cable connection leads arranged on another end of the flexible printed board and respectively connected to the plurality of inner leads, wherein the rigid substrate and the flexible printed board are arranged in a projection plane in an optical axis direction of the semiconductor package, and the plurality of third connection lands are arranged along one side of the rigid substrate.

2. The imaging unit according to claim 1, wherein the semiconductor package includes four connection terminals, the four connection terminals respectively having a power supply function, a grounding function, a first communication function and a second communication function, a rigid substrate includes four first connection lands respectively connected to the four connection terminals, the electronic component mount region includes two second connection lands on which the capacitor is mounted, the inner lead mount region includes four third connection lands, the flexible printed board includes four inner leads extended from one end of the flexible printed board in a bent manner and respectively connected to the four third connection leads in the inner lead mount region, and four cable connection leads arranged on the other end of the flexible printed board and respectively connected to the four inner leads, and the four third connection lands are arranged along the one side of the rigid substrate.

3. The imaging unit according to claim 2, wherein the two second connection lands are respectively connected to the connection terminals having the power supply function and the grounding function, and the four third connection lands are respectively connected to the connection terminals having the power supply function, the grounding function, the first communication function, and the second communication function.

4. The imaging unit according to claim 2, wherein the two second connection lands are arranged at positions overlapping with two of the four first connection lands in the optical axis direction, and are connected to the two of the four first connection lands at minimum distances via through holes or vias.

5. The imaging unit according to claim 2, further comprising four cables that are respectively connected to the four cable connection lands, wherein the cables are arranged in the projection plane in the optical axis direction of the semiconductor package.

6. The imaging unit according to claim 2, wherein two of the four third connection lands are arranged at positions overlapping with two of the four first connection lands in the optical axis direction, and connected to the two of the four first connection lands at minimum distances via through holes or vias.

7. An endoscope comprising:

an insertion portion; and the imaging unit according to claim 1 provided at a distal end of the insertion portion.

* * * * *